United States Patent [19]

Monin et al.

[11] Patent Number: Plant 5,801

[45] Date of Patent: Nov. 18, 1986

[54] CHERRY ROOTSTOCK-GM9 CULTIVAR

[75] Inventors: André Monin, Namur; Richard Trefois, Charleroi, both of Belgium

[73] Assignee: N.V. Jo Nicolai & Co., Duras, Belgium

[21] Appl. No.: 603,940

[22] Filed: Apr. 26, 1984

[51] Int. Cl.[4] ..... A01H 5/00

[52] U.S. Cl. ..... Plt./37

[58] Field of Search ..... Plt./37

[56] References Cited

U.S. PATENT DOCUMENTS

P.P. 4,059 6/1977 Tydeman ..... Plt./37

P.P. 5,159 12/1983 Tydeman ..... Plt./37

*Primary Examiner*—James R. Feyrer

*Attorney, Agent, or Firm*—Cushman, Darby & Cushman

[57] ABSTRACT

A new and distinct cultivar of cherry tree useful as a dwarfing cherry rootstock, substantially as shown and described, obtained from a selection of a seedling by crossing *Prunus incisia* with *Prunus serrula* at De Belder Nursery, Klamthough, Belgium, with, when used as an understock, induces less growth of the cherry tree and early flowering, is graft-compatable with cultivars of *Prunus avium* and *Prunus cerasus.*

3 Drawing Figures

BACKGROUND OF THE INVENTION

This new and distinct cultivar of cherry rootstock was obtained by selection of a hybrid resulting from crossing the known species *Prunus incisa* and *Prunus serrula* at De Belder Nursery, Klamthout, Belgium.

It has since been vegetatively propagated at the same place, both by herbaceous cutting under mist propagation, and by micropropagation in vitro.

The hybrid can be distinguished from its parents by a development which can be considered as intermediate between "*Prunus serrula*" and "*Prunus incisa*", by leaves which are larger than those of "*Prunus serrula*" and smaller than "*Prunus incisa*".

SUMMARY OF THE INVENTION

The new and distinct cultivar of cherry rootstock resulting from a cross between *Prunus incisa* and *Prunus serrula,* which has been given the designation GM 9 (in which the initial letters stand for Grand Manil, the Belgian experimental station) is of semi-upright growing type, and has a tendency to produce dwarf trees which flower early.

BRIEF DESCRIPTION OF THE DRAWINGS

The accompanying drawings show typical specimens of the new and distinct cultivar of cherry rootstock, wherein.

DETAILED DESCRIPTION

Figure 1:
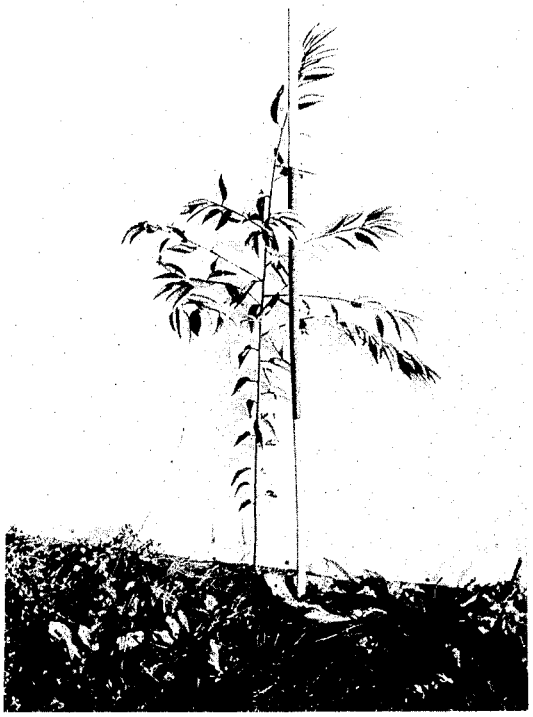
FIG. 1 shows a bough, with leaves, of the new cultivar of cherry rootstock.
Figure 3:
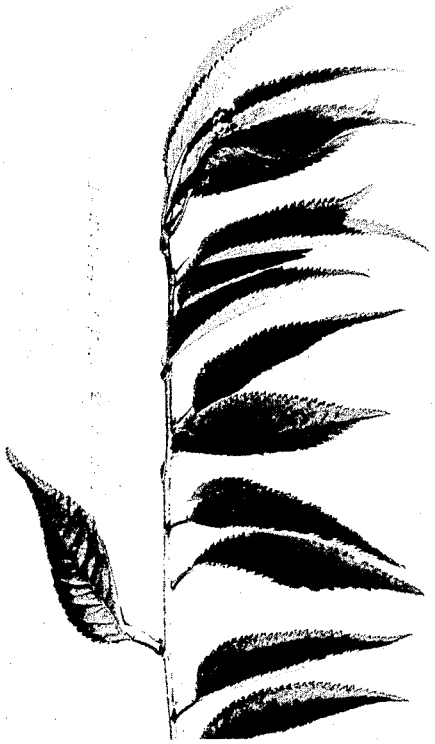
FIG. 3 shows three bough segments thereof, before budding.
Figure 2:
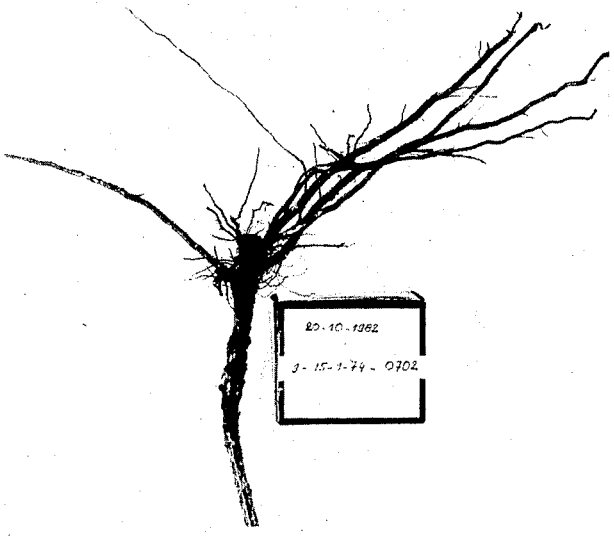
FIG. 2 shows an upper face of a leaf thereof on a larger scale.
Figure 4:
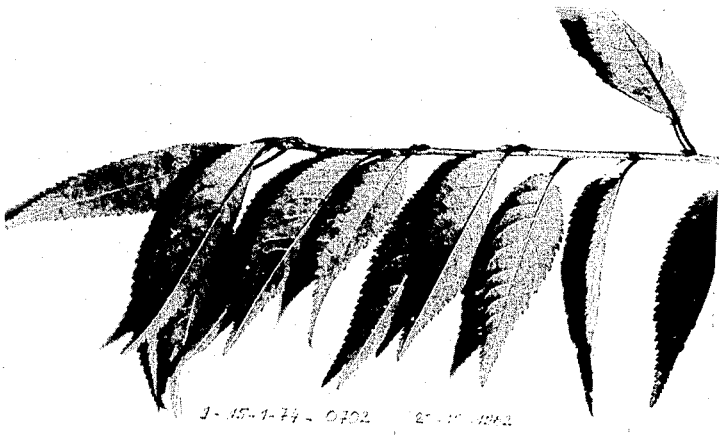
Figure 5:
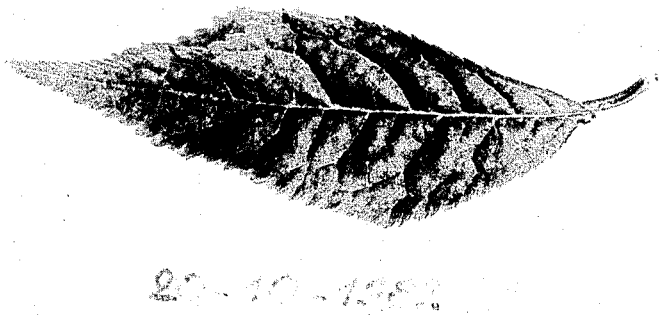
Figure 6:
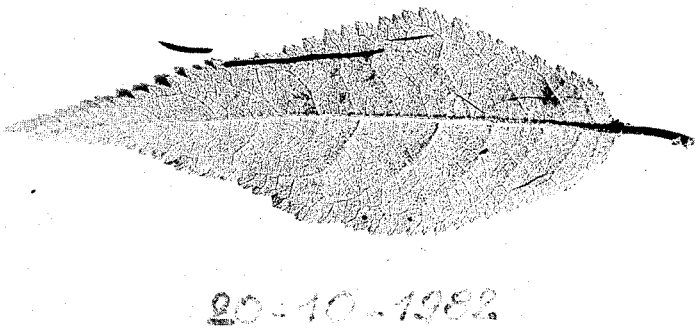
Figure 7:
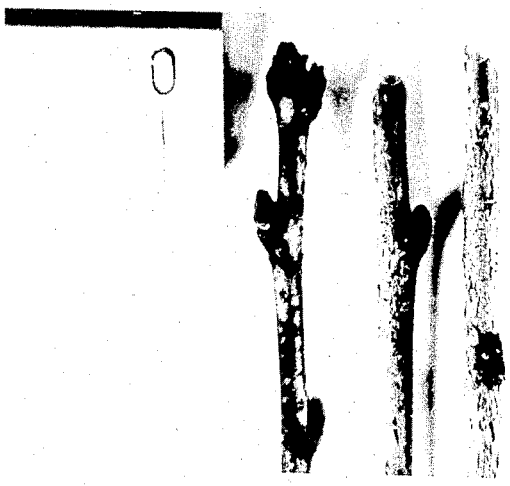
Figure 8:
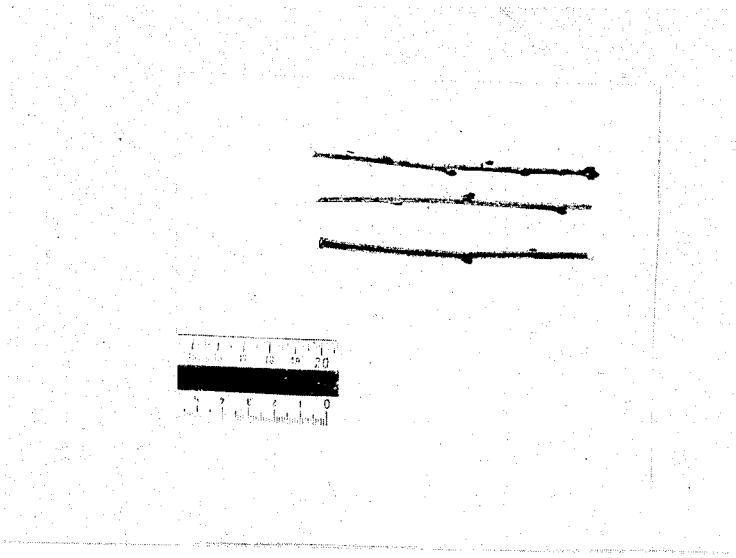
Figure 9:
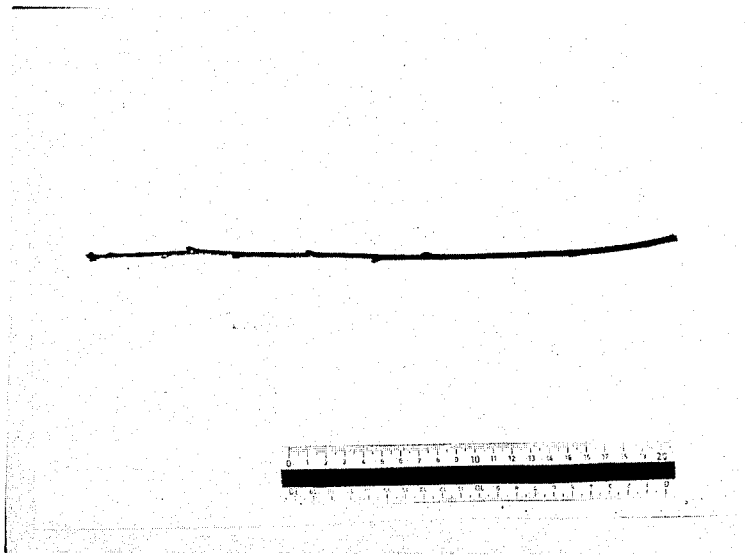

The new cultivar serves as a support for other cherry tree cultivars grafted thereon. Accordingly, the flowers, fruit and seed produced on the rootstock depend on the characteristics of the cherry tree cultivars which are grafted thereon. The characteristics of the inflorescence, fruit and seed produced by the new cultivar have not been systematically observed, because the mother plants were in the juvenile state.

The rootstock is semi-upright and shows a weak vigor. The cylindrical stem which is brown-gray at the base and reddish at the apex, which is typical of the Prunus species. It shows a few small lenticels.

The shape of the unbudded GM 9 tree is triangular, with the apex turned towards the soil. The adult size reaches a height of about 2 meters with a canopy that is less than 2 meters in diameter. The angles of the branches off the trunk are sharp (less than 45°). The leaves are small with a lanceolate form and an acuminate apex, the angle of which is sharp (20°). The base of the leaf is sharp pointed.

The ratio length to width of the leaf is higher than 2.1 to 1. The greatest width is situated under the middle of the leaf.

The leaf margin is serrated, with minute serrations occurring on each tooth of the margin. The leaf ends in a point with a gradual transition.

The leaves are green and lustreless.

The leaf petiole is short, the ratio length of the leaf to length of the leaf petiole is higher than 4 to a decimal point 3/1. The leaf is about 9–10 centimeters in length and about 3–3.5 centimeters in breadth.

The veins of the leaves are pennate, the lateral veins terminate shortly before the edge of the leaf with a tendency to inflex in the proximity of same.

Glands on the leaf petiole are very small. They are located on the upper part of the petiole, adjacent the leaf, but are almost invisible to the naked eye.

The internodes of the twig are short. The auxiliary buds at the base of the leaves are small, their apices are neither sharp pointed nor rounded off, few diverge from the stem and are very thin, their ratio of length to width lies in the range of 1.5 to 1. The spots where the leaves are implanted are projecting, the scale scars left by the falling of the leaves are reduced. The leaf scale scars are triangular, with an apex projecting laterally. The leaf scale scar is marked by three small, whitish dots.

Physiology

Weak vigor; late budding; semilate fall of the leaves; foliage has a yellowish color in autumn;

The ultimate sizes of trees grafted on GM 9 rootstock are about 2.5 meters in height and about 2.0 meters in diameter.

Good graft compatibility with cultivars of *Prunus avium* and *Prunus cerasus;* for instance sweet cherries: Early Rivers, Hedelfinger, Burlat, Schneider, Van and Merton Glory; and acid cherries: Montmorency, Schatten Morelle, and common sour cherry.

No or little suckering under cultivation, after grafting.

Resistance to winter cold

Acceptable in areas with a moderate climate.

Propagation

By herbaceous cutting under mist-propagation and by micropropagation in vitro.

The plants root well, and show a creeping rooting.

The plant can easily be grown as a scion in nurseries.

Vigor

Grafted on cultivars of "*Prunus avium*" and "*Prunus cerasus*", the plants show weak vigor. These characteristics were ascertained by an open field experience over more than 10 years. Fruits appear early. The stocks are made healthier by thermotherapy.

The cherry rootstock according to the invention is proposed as a very dwarfing stock for sweet and sour cherry cultivars, which permits high density orchards.

We claim:

1. A new and distinct cultivar of cherry tree useful as a dwarfing cherry rootstock, substantially as shown and described, obtained from a selection of a seedling by crossing *Prunus incisia* with *Prunus serrula* at De Belder Nursery, Klamthough, Belgium, with, when used as an understock, induces less growth of the cherry tree and early flowering, is graft-compatable with cultivars of *Prunus avium* and *Prunus cerasus.*

* * * * *